(12) United States Patent
Kobayashi et al.

(10) Patent No.: US 10,691,147 B2
(45) Date of Patent: Jun. 23, 2020

(54) SIMULATION METHOD, SIMULATION APPARATUS, AND PROGRAM

(71) Applicant: SUMITOMO HEAVY INDUSTRIES, LTD., Tokyo (JP)

(72) Inventors: Yoshitaka Kobayashi, Kanagawa (JP); Daiji Ichishima, Kanagawa (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 82 days.

(21) Appl. No.: 16/040,969

(22) Filed: Jul. 20, 2018

(65) Prior Publication Data

US 2019/0107852 A1    Apr. 11, 2019

(30) Foreign Application Priority Data

Oct. 6, 2017   (JP) .................................. 2017-195751

(51) Int. Cl.
*G05D 23/19*   (2006.01)
*G05B 17/02*   (2006.01)
(Continued)

(52) U.S. Cl.
CPC ......... *G05D 23/1917* (2013.01); *G05B 17/02* (2013.01); *G05D 23/19* (2013.01);
(Continued)

(58) Field of Classification Search
None
See application file for complete search history.

(56) References Cited

U.S. PATENT DOCUMENTS

2010/0042266 A1*  2/2010  Barhen ............... C10M 171/00
                                                        700/304
2010/0169062 A1*  7/2010  Linn .................... B29C 45/7693
                                                        703/2

(Continued)

FOREIGN PATENT DOCUMENTS

EP   2 899 655 A1   7/2015
JP   H10-334076 A   12/1998
JP   2006-285866 A  10/2006

OTHER PUBLICATIONS

Li et al., On multiscale non-equilibrium molecular dynamics simulations, Int. J. Numer. Meth. Engng (2010), 41 pages (Year: 2010).*

(Continued)

*Primary Examiner* — Jason Lin
(74) *Attorney, Agent, or Firm* — Michael Best & Friedrich LLP

(57) ABSTRACT

In simulating a behavior of a particle system including a plurality of particles disposed in an analysis region, by using a molecular dynamics method, centroid velocities of the particles present in a local region including a particle of interest are converted on the basis of the number of particles present in the local region for each of the particles, and thus a conversion value of a centroid velocity of the local region is calculated. Temperature control of maintaining the temperature of the particle system to be a target temperature is performed by using a difference between a velocity of the particle and the conversion value of the centroid velocity of the local region including the particle as a velocity of the particle which is a basis for calculating the temperature of the particle system.

6 Claims, 5 Drawing Sheets

(51) Int. Cl.
*G16C 10/00* (2019.01)
*G16C 60/00* (2019.01)
*G06F 30/20* (2020.01)
*G06F 111/10* (2020.01)

(52) U.S. Cl.
CPC ............. *G06F 30/20* (2020.01); *G16C 10/00* (2019.02); *G16C 60/00* (2019.02); *G06F 2111/10* (2020.01)

(56) References Cited

U.S. PATENT DOCUMENTS

2011/0246167 A1\* 10/2011 Ichishima .............. G16C 10/00
  703/11
2015/0186573 A1\* 7/2015 Ohnishi ................. G01N 15/10
  703/2
2017/0132048 A1\* 5/2017 Suwa .................. G06F 17/5009

OTHER PUBLICATIONS

Search report issued in European Application No. 18183583.6, dated May 6, 2019.

\* cited by examiner

→ $V_{g,i}$: CENTROID VELOCITY

SIMULATION METHOD, SIMULATION APPARATUS, AND PROGRAM

RELATED APPLICATIONS

Priority is claimed to Japanese Patent Application No. 2017-195751, filed Oct. 6, 2017, the entire content of which is incorporated herein by reference.

BACKGROUND

Technical Field

A certain embodiment of the present invention relates to a simulation method, a simulation apparatus, and a program.

Description of Related Art

A simulation method of performing temperature control according to a molecular dynamics method is well-known. For example, a velocity of a particle calculated according to the molecular dynamics method is updated on the basis of a desired setting temperature and a temperature of a system.

SUMMARY

In the kinetic theory of molecules, the temperature of a system including a plurality of molecules and an average value of kinetic energy of the plurality of molecules are associated with each other by using a Boltzmann constant. Since the temperature does not depend on an inertial system, in a case where a fluid system is analyzed, it is necessary to calculate kinetic energy of a molecule on the basis of a value obtained by subtracting the centroid velocity of the system from the velocity of each molecule when the temperature of the system is calculated.

Generally, in a case where a centroid velocity is obtained at a position of a certain particle, the centroid velocity is obtained on the basis of an average velocity of a particle group in the vicinity (local region) of the particle. However, in a case where a plurality of particles are in a gaseous state, a particle density is low, and thus other particles are not present around a single particle. In other words, only a single particle of interest is present within a local region. In this case, a centroid velocity at a position of the particle of interest is the same as a velocity of the particle. A difference between the velocity of the particle and the centroid velocity at the position is zero, and thus a calculated temperature also becomes zero. Thus, appropriate temperature control cannot be performed.

It is desirable to provide a simulation method, a simulation apparatus, and a program capable of performing temperature control even in analysis of a particle system of which a particle density is low and which is fluid, for example, as in a gaseous state.

According to an aspect of the present invention, there is provided a simulation method of simulating a behavior of a particle system including a plurality of particles disposed in an analysis region, by using a molecular dynamics method, the simulation method including: converting centroid velocities of the particles present in a local region including a particle of interest on the basis of the number of particles present in the local region for each of the particles, so as to calculate a conversion value of a centroid velocity of the local region; and performing temperature control of maintaining the temperature of the particle system to be a target temperature by using a difference between a velocity of the particle and the conversion value of the centroid velocity of the local region including the particle as a velocity of the particle which is a basis for calculating the temperature of the particle system.

According to another aspect of the present invention, there is provided a simulation apparatus including a processor that simulates a behavior of a particle system including a plurality of particles disposed in an analysis region, by using a molecular dynamics method, in which the processor has a function of acquiring an initial condition and a boundary condition for simulation, and a target temperature of the particle system from an input device, a function of simulating a behavior of the particle system on the basis of the input initial condition and boundary condition, a function of converting centroid velocities of the particles present in a local region including a particle of interest on the basis of the number of particles present in the local region for each of the particles, so as to calculate a conversion value of a centroid velocity of the local region, and performing temperature control of maintaining the temperature of the particle system to be a target temperature by using a difference between a velocity of the particle and the conversion value of the centroid velocity of the local region including the particle as a velocity of the particle which is a basis for calculating the temperature of the particle system, and a function of outputting a simulation result to an output device.

According to still another aspect of the present invention, there is provided a computer readable medium storing a program that causes a computer to realize a function of simulating a behavior of a particle system including a plurality of particles disposed in an analysis region, by using a molecular dynamics method, the program having: a function of simulating a behavior of the particle system on the basis of a given initial condition and boundary condition; and a function of converting centroid velocities of the particles present in a local region including a particle of interest on the basis of the number of particles present in the local region for each of the particles, so as to calculate a conversion value of a centroid velocity of the local region, and performing temperature control of maintaining the temperature of the particle system to be a target temperature by using a difference between a velocity of the particle and the conversion value of the centroid velocity of the local region including the particle as a velocity of the particle which is a basis for calculating the temperature of the particle system.

It is possible to perform temperature control even in analysis of a particle system of which a particle density is low and which is fluid, for example, as in a gaseous state.

DETAILED DESCRIPTION

Prior to description of an embodiment, a description will be made of a general temperature calculation method and a problem thereof for a particle system including a plurality of particles which are simulation targets in a molecular dynamics method with reference to FIGS. 1A to 2B.

In the kinetic theory of molecules, a relationship between kinetic energy of a molecule and a temperature is expressed by the following equation.

$$\frac{1}{N}\sum_{i}^{N}\frac{1}{2}m_i v_i^2 = \frac{3}{2}k_B T \tag{1}$$

Here, N is the number of particles, mi is the mass of a particle i, vi is a velocity of the particle i, T is the temperature of the particle system, and $k_B$ is a Boltzmann constant. In the molecular dynamics method, in order to realize a particle system with a target temperature, the temperature T of the particle system is frequently obtained by using Equation (1).

Since the temperature of the system does not depend on an inertial system, in a case where a fluid particle system of which the centroid moves is analyzed, it is necessary to use a value obtained by subtracting a centroid velocity of the particle system from a velocity of each particle when the temperature T of the particle system is obtained.

Figure 1A:
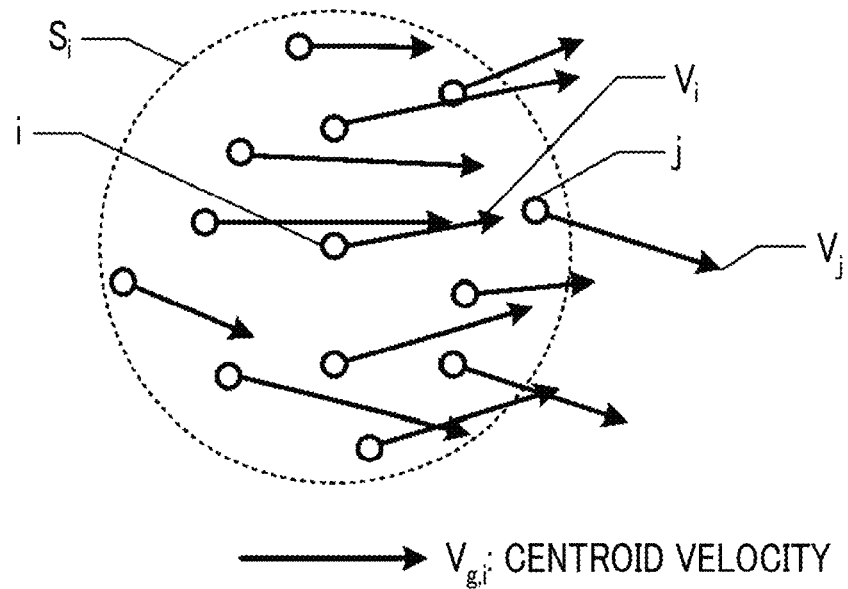
FIG. 1A is a schematic diagram illustrating velocities of a particle and a plurality of particles located in the vicinity (a local region centering on a position of the particle) thereof.

FIG. 1A is a schematic diagram illustrating velocities of a particle i and a plurality of particles j located in the vicinity (a local region $S_i$ centering on a position of the particle i) thereof. If the number of particles j (including the particle i) present in the local region $S_i$ is indicated by $n_i$, and a velocity of each of the particles j is indicated by $v_j$, a centroid velocity (hereinafter, referred to as a centroid velocity of the local region $S_i$) $V_{g,i}$ of the particle j present in the local region $S_i$ may be computed according to the following equation.

$$V_{g,i} = \frac{1}{n_i}\sum_{j \in S_i}^{n_i} v_j \tag{2}$$

Figure 1B:
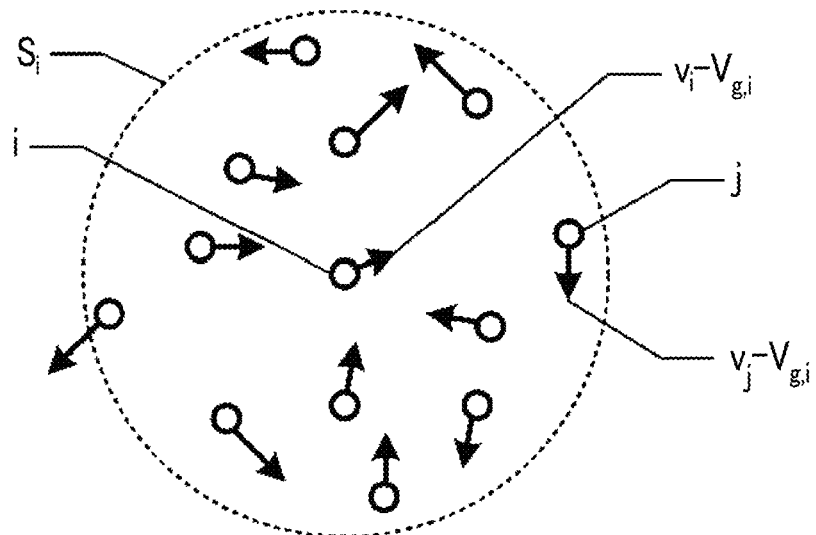
FIG. 1B is a schematic diagram illustrating a relative velocity for a centroid velocity, of the particle present in the local region.

FIG. 1B is a schematic diagram illustrating a relative velocity $v_j - V_{g,i}$ for the centroid velocity $V_{g,i}$ of the particle j present in the local region $S_i$. An average of the relative velocity $v_j - V_{g,i}$ is zero. The temperature T of the particle system may be obtained on the basis of the following equation.

$$\frac{1}{N}\sum_{i}^{N}\frac{1}{2}m_i(v_i - V_{g,i})^2 = \frac{3}{2}k_B T \tag{3}$$

Equation (3) indicates that, when the temperature T of the particle system is obtained, as a velocity of the particle i, a value obtained by subtracting the centroid velocity $V_{g,i}$ of the local region $S_i$ centering on a position of the particle i is subtracted from the velocity vi of the particle i is used.

Figure 2A:
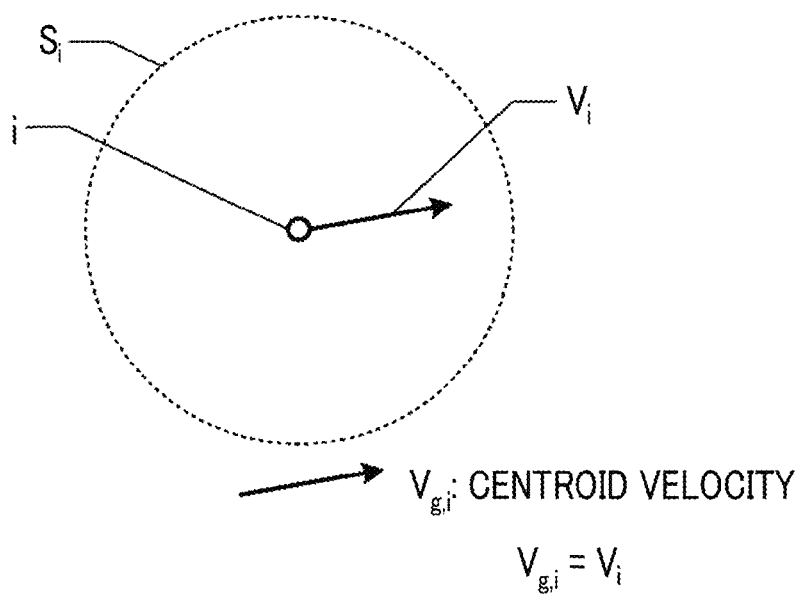
FIG. 2A is a schematic diagram illustrating a particle and a local region in a case of a state in which a particle density is low such as a gaseous state.

FIG. 2A is a schematic diagram illustrating the particle i and the local region $S_i$ in a case of a state in which a particle density is low such as a gaseous state. Since the particle density is low, only the particle i is present in the local region $S_i$. The centroid velocity $V_{g,i}$ of the local region $S_i$ in this case is the same as the velocity vi of the particle i.

Figure 2B:
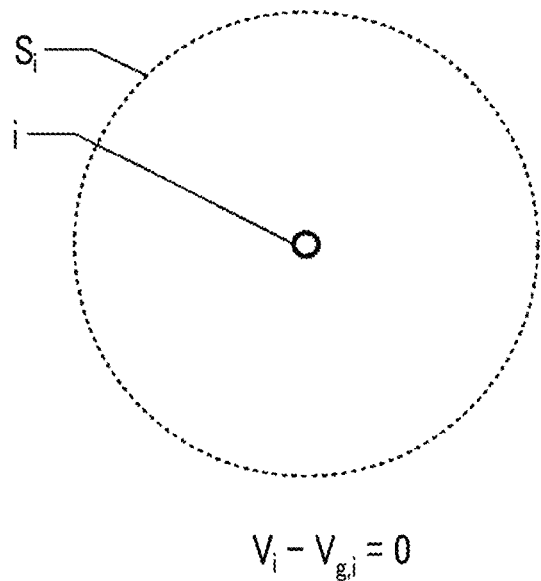
FIG. 2B is a schematic diagram illustrating a relative velocity for a centroid velocity, of the particle present in the local region.

FIG. 2B is a schematic diagram illustrating the relative velocity $v_i - V_{g,i}$ for the centroid velocity $V_{g,i}$ of the particle i present in the local region $S_i$. A relative velocity $v_i - V_{g,i}$ is zero. If the temperature T of the particle system in this case is obtained on the basis of Equation (3), the temperature T is zero. Even in a case where the number of particles $n_i$ in the local region $S_i$ is not 1, if the number of particles $n_i$ is small, the temperature T is estimated to be lower than an actual temperature. Thus, appropriate temperature control cannot be performed in simulation based on the molecular dynamics method.

Next, with reference to FIGS. 3 to 5, a description will be made a simulation method according to an embodiment of being capable of performing appropriate temperature control.

Figure 3:
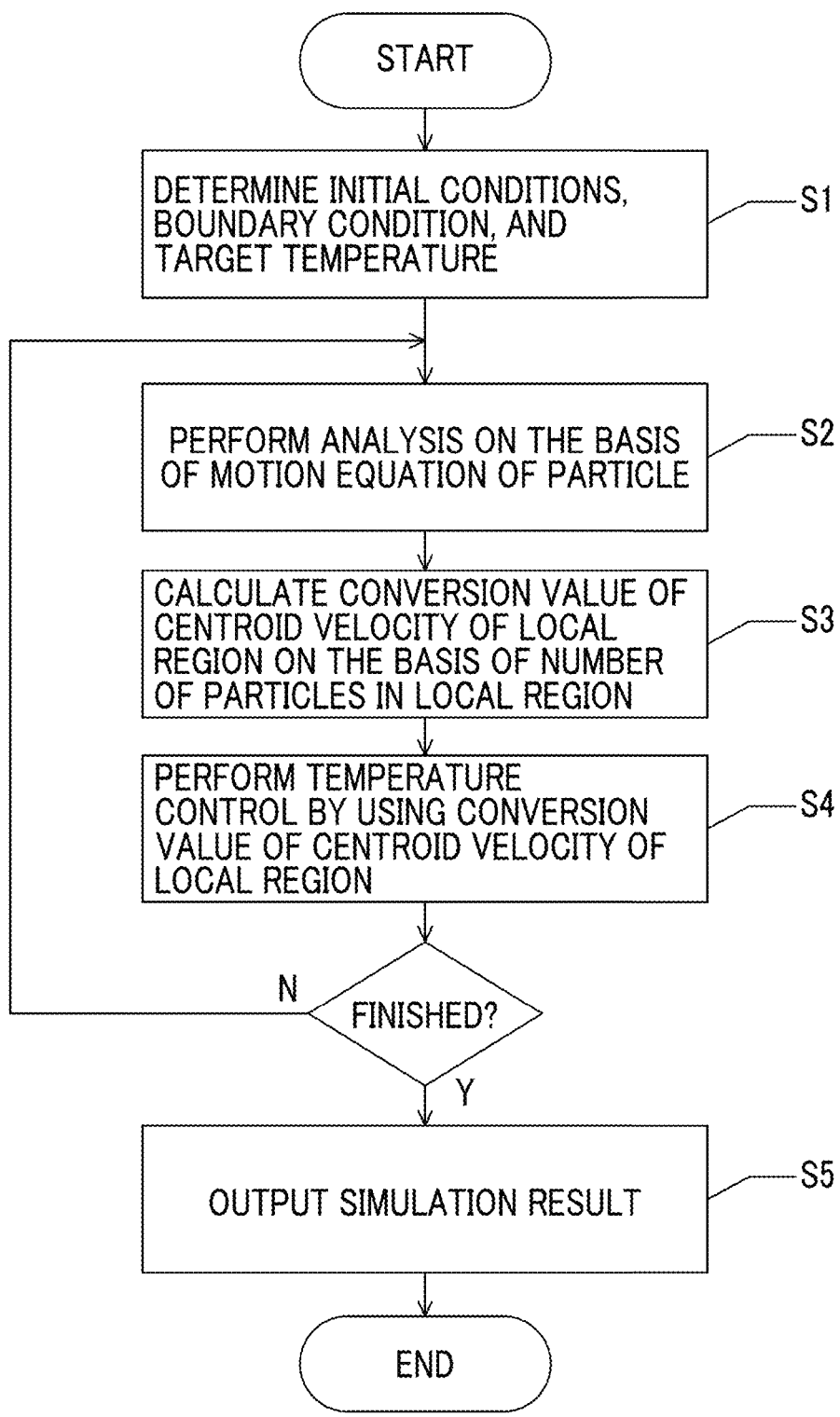
FIG. 3 is a flowchart illustrating a simulation method according to an embodiment.

FIG. 3 is a flowchart illustrating a simulation method according to the embodiment. First, initial conditions, a boundary condition, and a target temperature in simulation are determined (step S1). The initial conditions include a position and a velocity of each particle of a particle system. As the boundary condition, for example, a cyclic boundary condition is applied. In the simulation, temperature control is performed such that the temperature T of the particle system is close to the target temperature.

Next, motion analysis is performed on the basis of a motion equation followed by a particle (step S2). For example, a Lennard-Jones potential may be used as an inter-molecular interaction potential. Through the motion analysis, a position and a velocity of a particle after one time step elapses are obtained.

Next, the centroid velocity $V_{g,i}$ of the local region $S_i$ including the particle i of interest is converted on the basis of the number of particles $n_i$ present in the local region $S_i$ for each particle forming the particle system, and thus a conversion value $W_{g,i}$ of the centroid velocity of the local region $S_i$ is calculated (step S3). For example, the conversion value $W_{g,i}$ of the centroid velocity is calculated on the basis of the following conversion rule.

$$W_{g,i} = \left(1 - \frac{1}{n_i^2}\right) \times V_{g,i} \tag{4}$$

If the conversion rule in Equation (4) is used, as the number of particles $n_i$ present in the local region $S_i$ becomes smaller, the conversion value $W_{g,i}$ of the centroid velocity becomes closer to zero. If the number of particles $n_i$ is 1, the conversion value $W_{g,i}$ of the centroid velocity is zero. If the number of particles $n_i$ increases, the conversion value $W_{g,i}$ of the centroid velocity is close to the centroid velocity $V_{g,i}$. If the number of particles $n_i$ is infinity, the conversion value $W_{g,i}$ of the centroid velocity is the same as the centroid velocity $V_{g,i}$.

Next, temperature control is performed by using the conversion value $W_{g,i}$ of the centroid velocity of the local region $S_i$ (step S4). The temperature T of the particle system is calculated according to the following equation.

$$\frac{1}{N}\sum_{i}^{N}\frac{1}{2}m_i(v_i - W_{g,i})^2 = \frac{3}{2}k_B T \qquad (5)$$

For example, a Langevin method may be used for temperature control. In the Langevin method, temperature control is performed by applying random force and dissipative force to a particle. The Langevin method is described in J. M. Thijssen, "Computational Physics", Maruzen Publishing Co., Ltd. (2003), pages 204 to 208.

The processes from step S2 to step S4 are repeatedly performed by the number of time steps to be executed, and then a simulation result is output (step S5). The number of time steps to be executed is set in advance.

Simulation was actually performed for a particle system in which water droplets and water vapor coexist.

Figure 4:
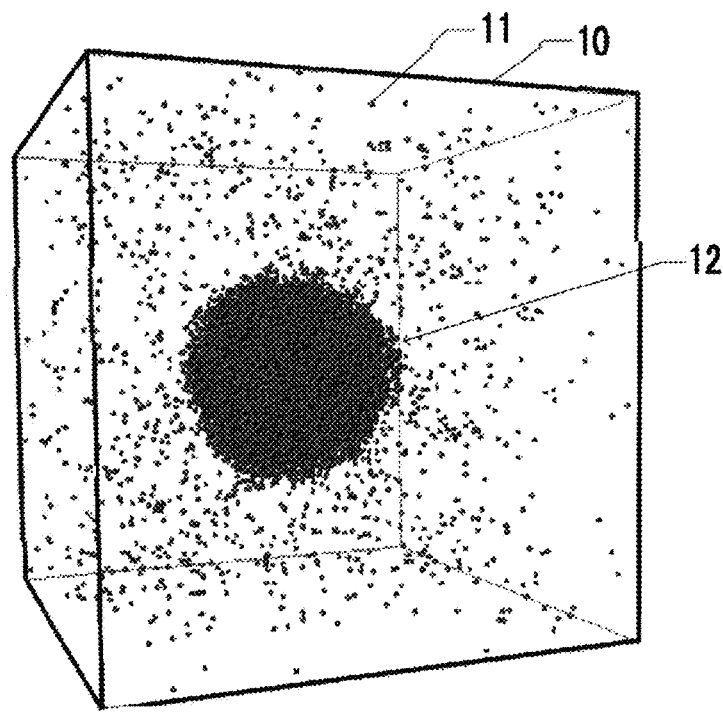
FIG. 4 is a schematic diagram illustrating a particle system which is a simulation target.

FIG. 4 is a schematic diagram illustrating a simulation target particle system. A plurality of particles 11 are disposed in a cubic analysis region 10. A region having a high particle density is present at the substantial center of the analysis region 10. The region having the high particle density corresponds to a water droplet 12. The particles 11 in a water vapor state are present in a region having a low particle density around the water droplet 12. Cyclic boundary conditions were applied to front, rear, upper, lower, left, and right boundaries of the analysis region 10. The number of particles was 8000, and a target temperature of the particle system was 300 K.

The following Lennard-Jones potential was used as an inter-molecular interaction potential U(r).

$$U(r) = 4\varepsilon\left[\left(\frac{\sigma}{r}\right)^{12} - \left(\frac{\sigma}{r}\right)^{6}\right] \qquad (6)$$

Here, ε and σ are fitting parameters. In the present simulation, values obtained by supposing water molecules were used as ε and σ. Specifically, ε was 404.52 K, and σ was 0.264 nm. The mass mi in Equation (5) was 18.02 Da. A resistance coefficient was 0.1τ. Here, τ is defined in the following equation.

$$\tau = \sigma\sqrt{\frac{m_i}{\varepsilon}} \qquad (7)$$

A sphere of which a radius is a distance at which particles produce interaction was as the local region $S_i$.

Figure 5:
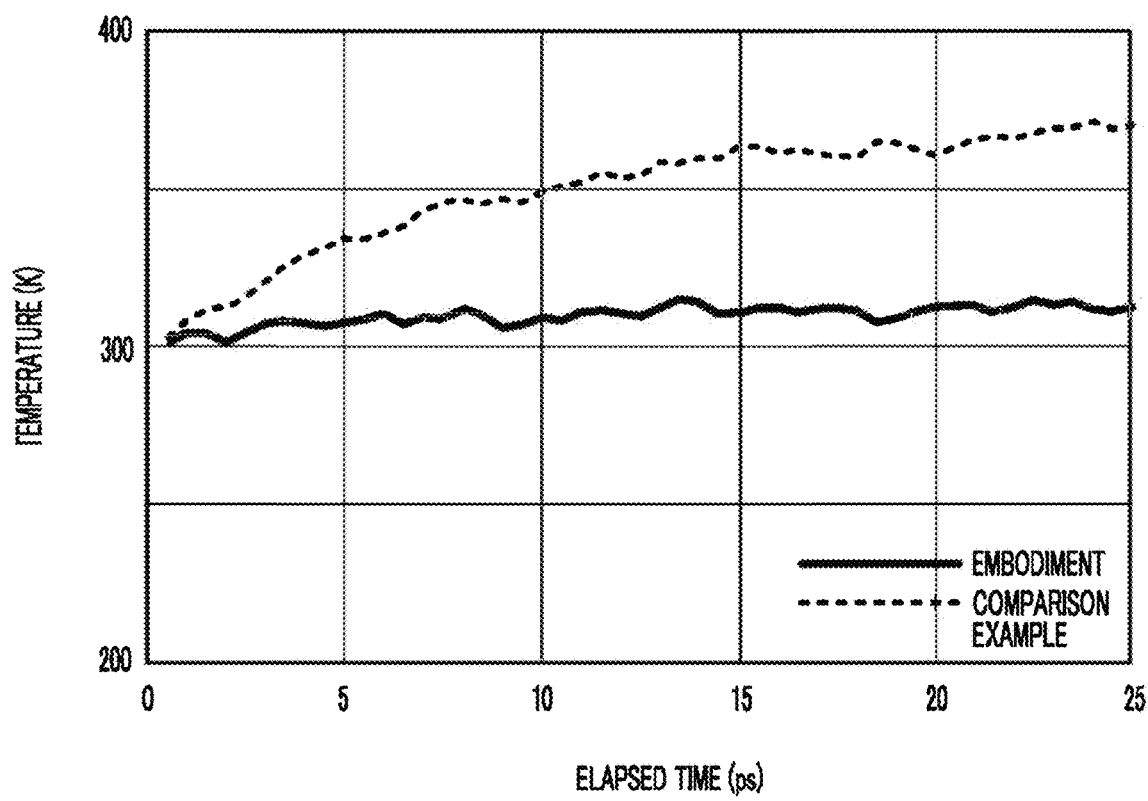
FIG. 5 is a graph illustrating a temporal change of the temperature of the particle system, calculated through simulation, through comparison with a comparison example.

FIG. 5 is a graph illustrating a temporal change of the temperature T of the particle system, calculated through simulation, through comparison with a comparison example. A transverse axis expresses an elapsed time in the unit "ps", and a longitudinal axis expresses the temperature T in the unit "K". In the graph in FIG. 5, a solid line indicates a result of simulation performed according to the method of the embodiment, and a dashed line indicates a result of simulation performed according to a comparison example. In the comparison example, the temperature T of the particle system was calculated by using Equation (3) without converting the centroid velocity $V_{g,i}$.

In the comparison example, a target temperature is set to 300 K, and temperature control for maintaining the temperature T of the particle system to be the target temperature is performed. However, it can be seen that the temperature T increases with the passage of time, and thus becomes distant from the target temperature. This is because the temperature T of the particle system is estimated to be lower than an actual temperature as described with reference to FIGS. 2A and 2B.

In a case where the simulation according to the present embodiment is used, it can be seen that the temperature T of the particle system is substantially maintained to be the target temperature of 300 K. As mentioned above, it is possible to perform appropriate temperature control by using the simulation according to the embodiment.

Next, modification examples of the embodiment will be described. In the embodiment, Equation (4) is used as the conversion value $W_{g,i}$ of a centroid velocity which is a basis for calculating the temperature T of a particle system, but the conversion value $W_{g,i}$ of a centroid velocity may be calculated according to other conversion rules. For example, a conversion rule may be used in which the conversion value $W_{g,i}$ of a centroid velocity of the local region $S_i$ monotonously increases as the number of particles $n_i$ present in the local region $S_i$ increases, and thus comes close to the centroid velocity $V_{g,i}$ of the local region $S_i$. A conversion rule may be used in which the conversion value $W_{g,i}$ of a centroid velocity is 0 if the number of particles $n_i$ present in the local region $S_i$ is 1, and comes gradually closer to the centroid velocity $V_{g,i}$ of the local region $S_i$ as the number of particles $n_i$ increases. The conversion rule in Equation (3) is an example of such a conversion rule.

In the embodiment, the Langevin method is used for temperature control, but other methods may be used. For example, a velocity of a particle may be scaled such that the temperature T of a particle system is maintained to be a target temperature. A Nose-Hoover method of giving a physically exact heat bath may be used.

In the embodiment, a sphere of which a radius is a distance at which the particle i substantially produces interaction was as the local region $S_i$, but other regions may be used as the local region $S_i$. For example, in a case where motion analysis in step S2 (FIG. 3) is performed, a region used as a region in which interaction with the particle i of interest is produced may be used as the local region $S_i$. The local region $S_i$ may include a region in which the particle i substantially produces interaction with other particles.

A renormalized molecular dynamics method (RMD method) as a result of developing a molecular dynamics method in order to be able to handle a macro-system has been proposed. The simulation method according to the embodiment may be applied to simulation using the renormalized molecular dynamics method. The renormalized molecular dynamics method may be considered to be an aspect of the molecular dynamics method, and, in the present specification, the "molecular dynamics method" is used as a generic concept including the "renormalized molecular dynamics method".

Next, with reference to FIG. 6, a description will be made of a simulation apparatus according to the embodiment. The simulation apparatus according to the embodiment includes a program causing a computer to execute the simulation method illustrated in FIG. 3, and executes the program.

Figure 6:
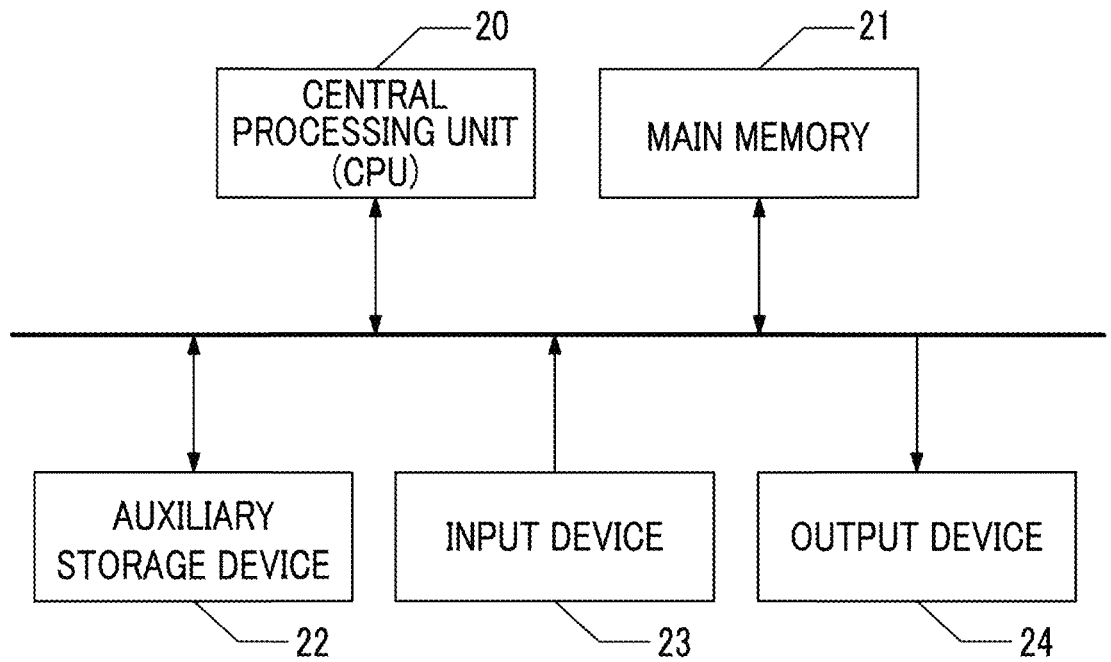
FIG. 6 is a block diagram illustrating a simulation apparatus according to the embodiment.

FIG. 6 is a block diagram illustrating the simulation apparatus according to the embodiment. As the simulation apparatus, a computer executing a simulation program may be used. The computer includes a central processing unit (CPU) 20, a main memory 21, an auxiliary storage device 22, an input device 23, and an output device 24. The auxiliary storage device 22 includes a recording medium in which a simulation program is stored. The recording medium may be built into the auxiliary storage device 22, and may be a removable medium which is attachable to and detachable from the auxiliary storage device 22. The simulation program is loaded to the main memory 21, and is executed by the CPU 20.

Information required for simulation is input from the input device 23. For example, various pieces of information which are set in step S1 (FIG. 3) are input. The CPU 20 acquires the initial conditions, the boundary condition, and the target temperature which are input from the input device 23. The CPU 20 outputs a simulation result to the output device 24. For example, in step S5 (FIG. 3), an image in which a behavior of a particle is visualized, a graph indicating a temporal change of a temperature of the particle system illustrated in FIG. 5, and the like are displayed on the output device 24.

The embodiment and the modification examples are only examples, partial replacement or combination of the configurations described in the embodiment and the modification examples may occur. The same advantageous effects based on the same configurations as those in the embodiment and the modification examples are not sequentially described in the embodiment and the modification examples. The process is not limited to the embodiment and the modification examples. For example, it is clear to a person skilled in the art that various alterations, modifications, combinations, and the like may occur.

It should be understood that the invention is not limited to the above-described embodiment, but may be modified into various forms on the basis of the spirit of the invention. Additionally, the modifications are included in the scope of the invention.

What is claimed is:

1. A simulation method of simulating a behavior of a particle system including a plurality of particles disposed in an analysis region, by using a molecular dynamics method, the simulation method comprising:
    converting centroid velocities of the particles present in a local region including a particle of interest on the basis of the number of particles present in the local region for each of the particles, so as to calculate a conversion value of a centroid velocity of the local region; and
    performing temperature control of maintaining the temperature of the particle system to be a target temperature by using a difference between a velocity of the particle and the conversion value of the centroid velocity of the local region including the particle as a velocity of the particle which is a basis for calculating the temperature of the particle system,
    wherein, as the number of particles present in the local region increases, the conversion value of the centroid velocity of the local region monotonously increases and comes closer to a centroid velocity of the particle present in the local region.

2. The simulation method according to claim 1, wherein the conversion value of the centroid velocity of the local region is 0 in a case where the number of particles present in the local region is 1, and comes closer to a centroid velocity of the particle present in the local region as the number of particles present in the local region increases.

3. The simulation method according to claim 1,
    wherein, if the particle of interest among the plurality of particles is indicated by i, a centroid velocity of the particle present in the local region is $V_{g,i}$, and the number of particles present in the local region is indicated by $n_i$, the conversion value $W_{g,i}$ of the centroid velocity is defined as $W_{g,i}=(1-(1/n_i^2))V_{g,i}$.

4. A simulation apparatus comprising:
    a processor that simulates a behavior of a particle system including a plurality of particles disposed in an analysis region, by using a molecular dynamics method,
    wherein the processor has
        a function of acquiring an initial condition and a boundary condition for simulation, and a target temperature of the particle system from an input device,
        a function of simulating a behavior of the particle system on the basis of the input initial condition and boundary condition,
        a function of converting centroid velocities of the particles present in a local region including a particle of interest on the basis of the number of particles present in the local region for each of the plurality of particles, so as to calculate a conversion value of a centroid velocity of the local region, and performing temperature control of maintaining the temperature of the particle system to be a target temperature by using a difference between a velocity of the particle and the conversion value of the centroid velocity of the local region including the particle as a velocity of the particle which is a basis for calculating the temperature of the particle system, and
        a function of outputting a simulation result to an output device,
    wherein, as the number of particles present in the local region increases, the conversion value of the centroid velocity of the local region monotonously increases and comes closer to a centroid velocity of the particle present in the local region.

5. The simulation apparatus according to claim 4, wherein the conversion value of the centroid velocity of the local region is 0 in a case where the number of particles present in the local region is 1, and comes closer to a centroid velocity of the particle present in the local region as the number of particles present in the local region increases.

6. The simulation apparatus according to claim 4,
    wherein, if the particle of interest among the plurality of particles is indicated by i, a centroid velocity of the particle present in the local region is $V_{g,i}$, and the number of particles present in the local region is indicated by $n_i$, the conversion value $W_{g,i}$ of the centroid velocity is defined as $W_{g,i}=(1-(1/n_i^2))V_{g,i}$.

* * * * *